United States Patent
Lipps et al.

(10) Patent No.: US 7,399,825 B2
(45) Date of Patent: Jul. 15, 2008

(54) SYNTHETIC PEPTIDE, INHIBITOR TO DNA VIRUSES

(76) Inventors: Binie V. Lipps, 4509 Mimosa Dr., Bellaire, TX (US) 77401; Frederick W. Lipps, 4509 Mimosa Dr., Bellaire, TX (US) 77401

( * ) Notice: Subject to any disclaimer, the term of this patent is extended or adjusted under 35 U.S.C. 154(b) by 555 days.

(21) Appl. No.: 10/745,876

(22) Filed: Dec. 24, 2003

(65) Prior Publication Data

US 2006/0142190 A1   Jun. 29, 2006

(51) Int. Cl.
*A61K 38/00* (2006.01)
*A61K 38/04* (2006.01)
*A61K 39/00* (2006.01)
*A61K 39/25* (2006.01)

(52) U.S. Cl. .................. 530/300; 530/327; 530/328; 530/330; 424/134.1; 424/229.1; 424/230.1

(58) Field of Classification Search ............ None
See application file for complete search history.

(56) References Cited

U.S. PATENT DOCUMENTS 5,648,339 A * 7/1997 Lipps et al. .............. 514/21

FOREIGN PATENT DOCUMENTS

WO       WO 00/58495      * 10/2000

OTHER PUBLICATIONS

Joubert et al Purification, Some Properties and Amino-Acid Sequences . . . from Najamja Kaouthia EurJBiochem 112,493-499 (1980).

* cited by examiner

*Primary Examiner*—Bruce R. Campell
*Assistant Examiner*—Sharon Hurt
(74) *Attorney, Agent, or Firm*—John R. Casperson

(57) ABSTRACT

The present invention relates to the identification of the active domain of Herpoxin, a DNA virus-inhibiting-protein which was isolated from cobra venom in U.S. Pat. No. 5,648,339 and has a molecular weight of 13.5 kDa We have isolated a fragment of Herpoxin which contains the active domain and which we have named Herp. Herp mimics the activity of Herpoxin in inhibiting the replication of DNA viruses. A synthetic version of the active fragment was produced having the amino acid sequence Asn-Leu-Tyr-Gln-Phe-Lys-Asn-Met-Ile-Gln. The synthetic version of Herp consisting of ten amino acids inhibits the replication of DNA viruses such as herpes viruses types 1 and 2, cytomegalovirus and varicella zoster virus as well as *Tubercle bacilli*.

13 Claims, No Drawings

SYNTHETIC PEPTIDE, INHIBITOR TO DNA VIRUSES

BACKGROUND OF THE INVENTION

In one aspect, this invention relates to the peptides which inhibit infectivity of DNA viruses and *T. bacillus*. In another aspect, this invention relates to the use of such peptides to treat infections caused by DNA viruses or *T. bacillus* in humans.

The earliest study on the interaction of snake venom toxins and viruses was reported by Sanders et al. In 1958 the same authors demonstrated the inhibition of Semiliki forest virus. Later in 1977 these investigators observed that the venom neurotoxin interfered with human strain of Poliomyelitis virus in Rhesus monkeys. Several investigators studied the inhibitory effects of venom toxins on various RNA viruses, to name a few; Murray encephalitis virus, Rous sarcoma and MH2 tumor viruses, Newcastle disease virus and influenza virus. However, no studies are reported on DNA viruses.

Herpes simplex viruses (HSV) type 1 and type 2 are double stranded DNA viruses. The clinical entities attributable to HSV-1 include the following: (1) Acute herpetic gingivostomatitis mostly in small children, (2) Eczema herpeticum-Kaposi's varicelliform eruption. Some times it can be fatal. (3) Keratoconjunctivitis infection of the eye, with recurrent infection, can lead to permanent opacification and blindness (4) Herpes encephalitis—carries a high mortality rate and the survivors often have residual neurological defects. (5) Herpes labilis—cold sores are most common recurrent disease in the form of oral lesions.

HSV-2 is implicated in the following: (1) Genital herpes, progenitalis, is characterized by vesiculoulcerative lesions of the penis or the cervix, vulva and vagina. (2) Neonatal herpes can be transmitted to the newborn during the birth by contact with herpetic lesions in the birth canal if the mother infected with the virus. Such transmission can produce permanent brain damage. Varicella zoster virus is a double-stranded DNA virus and it is morphologically identical with herpes simplex viruses. It is a causative agent for shingles in adults which is characterized by an inflammatory reaction of the posterior nerve roots and ganglia, accompanied by the affected sensory nerves.

Currently, there is no effective treatment against the infections caused by HSV viruses. Therefore, the synthetic active Herp has great potential as a therapeutic to treat infections caused by DNA viruses.

Currently, tuberculosis (TB) is a major global health problem and Herp is inhibitory to acid fast *Tubercle bacilli*. Effective treatments for TB are much sought after.

In our U.S. Pat. No. 5,648,339 we derived a DNA virus-inhibiting protein from snake venom which meets many of the above needs. We named this protein Herpoxin. However, because Herpoxin is derived from snake venom, it may not gain widespread acceptance and use. Also, because Herpoxin has a molecular weight of 13.5 kDa it cannot be easily synthesized and is somewhat limited in the ways it can be effectively administered. A synthetic peptide which mimics the properties of Herpoxin would be very desirable, and would have better capabilities for crossing the blood-brain barrier and coming into contact with pathogens in the central nervous system.

OBJECTS OF THE INVENTION

An object of the invention is to provide a synthetic peptide which mimics the inhibitory property of Herpoxin. Such peptides can be made in abundance to provide therapeutics for the infections caused by DNA viruses and tuberculosis. The bioavailability of such a small molecule having low molecular weight will react with the virus in the gut like chemical drugs without getting degraded and also may cross the blood-brain barrier to attack infections in the central nervous system. It is anticipated that the peptide will be another snake venom derived drug for human therapeutics besides the currently available anticoagulant, Ancrode, which is not used in the United States

SUMMARY OF THE INVENTION

In this invention, we isolated the active fragment of Herpoxin and it is shown in SEQ. ID. NO.: 1. In one aspect, this invention relates to a peptide which contains at least a three amino acid portion of SEQ. ID. NO.: 1 and no more than 25 amino acids total. We have named the most preferred embodiment of this peptide Herp.

In the most preferred embodiment, Herp is a synthetic peptide consisting of ten amino-acids from the N-terminal of SEQ. ID. NO.: 2, Asn-Leu-Tyr-Gln-Phe-Lys-Asn-Met-Iso-Gln. Synthetic Herp is characterized as a potent inhibitor of DNA viruses: HSV-1 HSV-2, cytomegalovirus (CMV) and varicella zoster viruses, when tested in cell cultures. Incorporation of 10 μg/ml of Herp in the medium inhibited the cytopathic effect (CPE) of the DNA viruses by two to four logs of tissue culture infectivity dose TCID/50, having no effect on the respective uninfected cells up to 200 μg/ml. Herp also inhibits the multiplication of *T. bacilli*. Incorporating Herp in the medium showed reduction in number of colonies of *T. bacilli*. Based upon results in cell culture, Herp in its synthetic form is proposed to treat diseases caused by DNA viruses, such as, oral and genital herpes legions, *Kaposi sarcoma* and tuberculosis. Herp can be administered orally, under the tongue, topically, by spray or by injection, or by any other means which brings an effective amount of it into contact with the pathogen.

DETAILED DESCRIPTION OF THE INVENTION

Isolation of Herpoxin, DNA Virus Inhibitor:

The DNA virus inhibitor Herpoxin (natural Herp) was isolated in purity from the venom of *Naja kaouthia*, Asian cobra snake, by high pressure liquid chromatography, having molecular weight 13.5 kDa. Purification of natural Herp from the venom of *Naja kaouthia*, Asian cobra snake, is described in the awarded U.S. Pat. No. 5,648,339, the disclosure of which is incorporated herein by reference. Incorporation of 10 μg/ml of natural Herp inhibited the cytopathic effects (CPE) of HSV viruses type 1 and 2, by two to four logs of tissue culture infectivity dose TCID/50, having no effect on the respective uninfected cells up to 200 μg/ml.

We realized that natural Herp derived from cobra venom will have lot of resistance from the FDA for human use. Therefore, efforts were made to identify the active domain of natural Herp and convert it to the synthetic version for human use. This patent is about the synthetic peptide Herp for treatment of infections caused by DNA viruses.

Identification of the Active Domain of Herpoxin by Trypsin Digestion: Purified homogeneous preparation of Herpoxin was treated with trypsin dissolved in 0.1 M ammonium bicarbonate buffer pH 8.0. Herpoxin and trypsin were mixed in 40:1 ratio, precisely 5 mg of Herpoxin to 0.25 mg trypsin. The mixture was incubated at 37° C. to cause fragmentation at arginine and lysine sites. After 18 hours of incubation the reaction was stopped by cooling the mixture at 4° C.

Separation of Fragments from Trypsin Digest: The trypsin digested fragments were separated on HPLC. Trypsin digested Herpoxin resolved into several different fragments. The fragments were collected individually and were dialyzed against water using 500 Dalton weight cutoff tubing (Spectrum USA). The protein concentration of each fragment was measured by using Bio-Rad (USA) protein kit and was adjusted to 100 µg/ml in 0.05 M phosphate buffered saline (PBS).

Biological Activity of Fragments: The inhibitory activity of the fragments was tested on African green monkey kidney Vero cells, infected with HSV-2 virus. Dulbecco Modified Eagle's Medium (DMEM) containing 10% newborn calf serum (NBCS), L-glutamine and the antibiotics penicillin and streptomycin was used to grow Vero cells into monolayers after being monodispersed with a mixture of trypsin/EDTA. Initially, each fraction was tested on monolayers of Vero cells grown in 48 well plate and infected at 10-2 dilution of HSV-2 virus. The virus was allowed to absorb for 1 hour at 37° C. in a humid CO2 incubator. The medium containing different concentrations such as 20, 10, 5, 2.5, and 1.0 µg/ml of each fraction was tested. Cells infected with virus received PBS to serve as positive controls, for virus CPE. The tests were read after six days. It was revealed that one of the fragments showed the highest inhibition of virus. This one was considered the HSV-2 virus inhibitor peptide, or the active domain of Herpoxin protein.

Synthesis of Herp: The most active fragment became Herp was sequenced for its amino-acids composition was found to consist of 13 amino acids. The sequence for the most active fragment from the N-terminal was found to be Asn-Leu-Tyr-Gln-Phe-Lys-Asn-Met-Ile-Gln-Gln-Phe-Leu. Synthetic Herp of 13 amino acids was constructed to provide SEQ ID. NO 1: Asn-Leu-Tyr-Gln-Phe-Lys-Asn-Met-Ile-Gln-Gln-Phe-Leu.

Two additional synthetic versions of Herp were made having 10 and 5 amino acids from the N-terminal. The Synthetic Herp of 10 amino acids provided SEQ ID. NO 2: Asn-Leu-Tyr-Gln-Phe-Lys-Asn-Met-Ile-Gln The synthetic Herp of 5 amino acids provided SEQ ID. NO 3: Asn-Leu-Tyr-Gln-Phe All versions displayed some antiviral activity. It was revealed that the synthetic peptide consisting of 10 amino acids, SEQ. ID. NO.: 2, exhibited the most inhibition of herpes viruses. The sequencing and synthesizing was contracted out to the Protein Core Laboratory of Baylor College of Medicine, Houston, Tex. The sequence of the most active synthetic version of Herp from N-terminal was found to be Asn-Leu-Tyr-Gln-Phe-Lys-Asn-Met-Ile-Gln (SEQ. ID No 2).

Infectivity Inhibition of HSV-1 and HSV-2 Viruses by Synthetic Herp: For comparison, Herpoxin and the synthetic Herps were tested in Vero cell cultures infected with HSV-1 or HSV-2 viruses. The cells were infected in serial concentrations from $10^2$ to $10^8$. Three wells were used for each concentration. After absorption of the virus the cultures were divided into three groups. Group one received medium containing PBS as a positive control, group two received medium containing 10 µg/ml of Herpoxin (natural Herp) and in the remaining group the medium was incorporated with 10 µg/ml synthetic Herp (Syn-Herp-10 amino acid (AA) version). The tests were read after six days and TCID/50 were calculated from CPE. The results are seen in Table I.

TABLE I

Log Inhibition of infectivity of HSV-1 and HSV-2 viruses in the presence of Nat Herp (Herpoxin) and Syn Herp (10 AA) at the concentration of 10 µg/ml in Vero cells.

| Virus | Additive | Log TCID/50 | Nat Herp | Syn Herp |
|---|---|---|---|---|
| HSV-1 | PBS | 5.2 | | |
| | Nat Herp | 3.1 | 2.1 | |
| | Syn Herp | 4.0 | | 1.2 |
| HSV-2 | PBS | 7.0 | | |
| | Nat Herp | 4.5 | 2.5 | |
| | Syn Herp | 5.1 | | 1.9 |

The results of Table I clearly show the inhibition of infectivity of HSV viruses in presence of synthetic Herp was comparable to Herpoxin (natural Herp). Log TCID/50 for HSV-1 was 5.2 and the infectivity inhibition for nat. Herp and syn. Herp 2.1 and 1.9 respectively. Giving the log TCID/50 infectivity inhibition 2.1 and 1.2 respectively. Similarly, the inhibition in the infectivity of HSV-2 by nat Herp was 2.5 versus 1.9 with syn. Herp. The inhibition of HSV viruses can be higher by increasing the concentration of syn Herp.

Discussion: Currently, there are drugs to treat herpes virus caused infections and tuberculosis in human. However, an increasing number of herpes virus and *T. bacilli* strains have become resistant to the existing drugs. Therefore, new therapeutics like Herp should be immensely applicable and useful. Herp can be administered topically, orally or by injection.

The class of peptides provided in accordance with the invention can be characterized as compositions of matter comprising a peptide containing no more than 25 amino acids total. Preferably, the peptide which contains at least a three amino acid portion of SEQ. ID. NO.: 1. More preferably, the peptide contains at least a 5 amino acid portion of SEQ. ID. NO.: 1 and no more than 20 amino acids total. A peptide as shown in SEQ. ID. NO.: 3 or a peptide beginning with SEQ. ID. No.: 3 at its N-terminal are exemplary. Most preferably, the peptide contains at least a 7 amino acid portion of SEQ. ID. NO.: 1 and no more than 15 amino acids total. Peptides as shown in SEQ. ID. NO.: 1 or SEQ. ID. NO.: 2, or beginning with SEQ. ID. NO. 1 or SEQ. ID. NO.: 2 at their N-terminals are exemplary.

The most preferred peptides are as those consisting essentially of SEQ. ID. Nos. 1, 2 and 3, because these have been tested with good results. The peptide in SEQ. ID. 2 was found to be the most active version tested of synthetic Herp.

We thus view one aspect of our broad invention as a method for treating a condition caused by DNA viruses and *T. bacilli* in humans. The method is carried out by identifying a patient suffering from a condition caused by a pathogen selected from DNA viruses and *T. bacilli*. The patients can be diagnosed by the usual clinician. The diagnosed patient is treated with synthetic Herp, such as the one consisting of ten amino acids as set forth in SEQ. ID. NO.: 2. The treatment is carried out in a manner effective to bring the peptide into contact with the pathogen.

Generally speaking the peptide Herp is administered in an amount of from about 0.01 to about 100 milligrams daily, preferably in an amount of from about 0.1 to about 10 milligrams daily. An amount in the range of 0.02 to 2 milligrams daily is also believed suitable. Functionally phrased, the peptide is administered in an amount sufficient to result in a concentration in the patient which high enough to inhibit the replication of DNA virus or *T. bacilli* but beneath a concentration which is toxic to the normal cells. The administration technique is selected from the group consisting of nasal insufflation, buccal administration, oral ingestion, intramuscular injection, intravenous injection, and topical application. For example, Herp can be suitably administered intravenously after being dispersed in a fluid.

It is believed that the invention will be effective to inhibit replication and multiplication of DNA viruses and *T. bacilli* respectively. While certain preferred embodiments of the invention have been described herein, the invention is not to be construed as being so limited, except to the extent that such limitations are found in the claims.

The invention claimed is:

1. A synthetic peptide molecule consisting of a portion of SEQ. ID. NO.: 1 which contains SEQ. ID. NO.: 2 beginning at the N-terminal.

2. A synthetic peptide molecule selected from the group consisting of SEQ. ID. NO.: 1 and a portion of SEQ. ID. NO.: 1 beginning with SEQ. ID. NO.: 3 at its N-terminal.

3. A synthetic peptide molecule as in claim 2 consisting of a portion of SEQ. ID. NO.: 1 wich contains SEQ. ID. NO.: 3 beginning at the N-terminal.

4. A synthetic peptide molecule as in claim 2 selected from the group consisting of SEQ. ID. NO.: 1, SEQ. ID. NO.: 2, and SEQ. ID. NO.: 3.

5. A synthetic peptide molecule as in claim 2 consisting of SEQ. ID. NO.: 2.

6. A method of using a peptide comprising administering the peptide of claim 2 to a patient who is infected with pathogen selected from the group consisting of HSV-1, HSV-2, *cytomegalovirus* and varicella zoster virus, in a manner effective to bring the peptide into contact with the pathogen.

7. A method as use as in claim 6 wherein the administration technique is selected from the group consisting of nasal insufflation, buccal administration, oral ingestion, intramuscular injection, intravenous injection, and topical application.

8. A method as in claim 6 wherein the peptide is administered intravenously after being dispersed in a fluid.

9. A method as in claim 6 wherein the peptide is administered in a manner to reach to the blood stream of said patient.

10. A method as in claim 6 wherein the peptide is capable of crossing the blood brain barrier.

11. A method of use as in claim 6 wherein the peptide is administered in an amount of from about 0.01 to about 100 milligrams daily.

12. A method as in claim 11, wherein the peptide is administered in amounts of from about 0.1 to about 10 milligrams daily.

13. A method as in claim 11 wherein the range of 0.02 to 2 milligrams of the peptide are administered on a daily basis.

* * * * *

```
                              SEQUENCE LISTING

<160> NUMBER OF SEQ ID NOS: 3

<210> SEQ ID NO 1
<211> LENGTH: 13
<212> TYPE: PRT
<213> ORGANISM: ARTIFICIAL
<220> FEATURE:
<223> OTHER INFORMATION: FRAGMENT OF PROTEIN ISOLATED FROM VENOM OF
      NAJA KAOUTHIA
<300> PUBLICATION INFORMATION:
<302> TITLE: HERPOXIN: HERPES VIRUS INHIBITOR AND METHOD
<310> PATENT DOCUMENT NUMBER: US 5,648,339
<312> PUBLICATION DATE: 1997-07-15
<313> RELEVANT RESIDUES: (1)..(13)

<400> SEQUENCE: 1

Asn Leu Tyr Gln Phe Lys Asn Met Ile Gln Gln Phe Leu
1               5                   10

<210> SEQ ID NO 2
<211> LENGTH: 10
<212> TYPE: PRT
<213> ORGANISM: ARTIFICIAL
<220> FEATURE:
<223> OTHER INFORMATION: SYNTHESIZED.  CORRESPONDS TO POSITIONS 1-10 OF
      SEQ. ID. NO.: 1

<400> SEQUENCE: 2

Asn Leu Tyr Gln Phe Lys Asn Met Ile Gln
1               5                   10

<210> SEQ ID NO 3
<211> LENGTH: 5
<212> TYPE: PRT
<213> ORGANISM: ARTIFICIAL
<220> FEATURE:
<223> OTHER INFORMATION: SYNTHESIZED.  CORRESPONDS TO POSITIONS 1-5 OF
      SEQ. ID. NO.: 1.

<400> SEQUENCE: 3

Asn Leu Tyr Gln Phe
1               5
```